US008012472B2

(12) United States Patent
Gomer et al.

(10) Patent No.: US 8,012,472 B2
(45) Date of Patent: *Sep. 6, 2011

(54) COMPOSITIONS AND METHODS FOR SUPPRESSING FIBROCYTES

(75) Inventors: Richard Gomer, Houston, TX (US); Darrell Pilling, Pearland, TX (US)

(73) Assignee: William Marsh Rice University, Houston, TX (US)

(*) Notice: Subject to any disclaimer, the term of this patent is extended or adjusted under 35 U.S.C. 154(b) by 445 days.

This patent is subject to a terminal disclaimer.

(21) Appl. No.: 11/535,649

(22) Filed: Sep. 27, 2006

(65) Prior Publication Data

US 2007/0065866 A1 Mar. 22, 2007

Related U.S. Application Data

(63) Continuation-in-part of application No. PCT/US2006/005229, filed on Feb. 15, 2006, and a continuation-in-part of application No. 11/158,966, filed on Jun. 22, 2005, now Pat. No. 7,666,432, which is a continuation-in-part of application No. PCT/US03/40957, filed on Dec. 22, 2003.

(60) Provisional application No. 60/436,046, filed on Dec. 23, 2002, provisional application No. 60/436,027, filed on Dec. 23, 2002, provisional application No. 60/515,776, filed on Oct. 30, 2003, provisional application No. 60/519,467, filed on Nov. 12, 2003, provisional application No. 60/525,175, filed on Nov. 26, 2003.

(51) Int. Cl.
*A61K 39/395* (2006.01)
(52) U.S. Cl. ....................... 424/130.1; 514/826; 514/885
(58) Field of Classification Search ......................... None
See application file for complete search history.

(56) References Cited

U.S. PATENT DOCUMENTS

| | | | |
|---|---|---|---|
| 4,233,969 A | 11/1980 | Lock et al. | 128/156 |
| 4,556,056 A | 12/1985 | Fischer et al. | 128/156 |
| 4,782,014 A | 11/1988 | Serban et al. | 435/7 |
| 5,092,876 A | 3/1992 | Dhawan et al. | 623/11 |
| 5,591,709 A | 1/1997 | Lindenbaum | 514/4 |
| 5,654,186 A | 8/1997 | Cerami et al. | 435/325 |
| 5,698,589 A | 12/1997 | Allen | 514/509 |
| 5,804,446 A | 9/1998 | Cerami et al. | 435/385 |
| 5,846,796 A | 12/1998 | Cerami et al. | 435/172.3 |
| 6,037,458 A | 3/2000 | Hirai et al. | 530/415 |
| 6,054,121 A | 4/2000 | Cerami et al. | 424/93.7 |
| 6,126,918 A | 10/2000 | Pepys et al. | 424/9.1 |
| 6,174,526 B1 | 1/2001 | Cerami et al. | 424/93.1 |
| 6,365,570 B1 | 4/2002 | Van Kessel et al. | 514/8 |
| 6,406,698 B1 | 6/2002 | Svehag et al. | 424/184.1 |
| 6,537,811 B1 | 3/2003 | Freier | 435/375 |
| 6,600,019 B2 | 7/2003 | Prayaga et al. | 530/350 |
| 6,872,541 B2 | 3/2005 | Mills | 435/7.21 |
| 2002/0058284 A1 | 5/2002 | Winkel | 435/7.1 |
| 2003/0003567 A1 | 1/2003 | Barber et al. | 435/235.1 |
| 2003/0022245 A1 | 1/2003 | Mills | 435/7.8 |
| 2004/0068095 A1 | 4/2004 | Shimkets et al. | 530/350 |
| 2005/0238620 A1 | 10/2005 | Gomer et al. | 424/85.2 |

FOREIGN PATENT DOCUMENTS

| | | |
|---|---|---|
| DE | 28 49 570 | 6/1980 |
| EP | 1 090 630 | 4/2001 |
| JP | 54-5023 | 1/1979 |
| JP | 11-319542 | 11/1999 |
| WO | 9941285 A | 8/1999 |
| WO | 99/45900 | 9/1999 |
| WO | 03031572 | 4/2003 |
| WO | 03097104 | 11/2003 |
| WO | 2004016750 | 2/2004 |
| WO | 2004016750 A2 | 2/2004 |
| WO | 2004058292 | 7/2004 |
| WO | 2004059318 | 7/2004 |
| WO | 2004059318 A2 | 7/2004 |
| WO | 2005110474 A | 11/2005 |
| WO | 2005115452 A2 | 12/2005 |
| WO | 2006002438 A2 | 1/2006 |

OTHER PUBLICATIONS

Ghazizadeh et al., Physical and Fuctional Association of Src-Related Protein Tyrosine Kinases with Fe Gamma-RII in Monocytic THP-1 Cells, Journal of Biological Chemistry 269, pp. 8878-8884, 1994.
Daeron, Fc Receptor Biology, Annual Review of Immunology 15, pp. 203-234, 1997.
Duchemin et al., Association of Non-Receptor Protein Tyrosine Kinases with the Fe Gamma RI/Gamma-Chain Complex in Monocytic Cells, J Immunol 158, pp. 865-871, 1997.
Korade-Mirnics et al., Src Kinase-Mediated Signaling in Leukocytes, J. Leukoc Biol 68, pp. 603-613, 2000.
Turner et al., Tyrosine Kinase SYK: Essential Functions for Immunoreceptor Signalling, Immunology Today 21, pp. 148-154, 2000.
Sada et al., Structure and Function of Syk Protein-Tyrosine Kinase, J Biochem (Tokyo) 130, pp. 177-186, 2001.
Tridandapani et al., Regulated Expression and Inhibitory Function of FcgammaRIIb in Human Monocytic Cells, Journal of Biological Chemistry, American Society of Biolochemical Biologists, Birmingham, vol. 277, No. 7, pp. 5082-5089, Feb. 15, 2002.
Bain et al., The Specificities of Protein Kinase Inhibitors: An Update, Biochem. J 371, pp. 199-204, 2003.
Lai et al., Potent Small Molecule Inhibitors of Spleen Tyrosine Kinase (Syk), Bioorganic & Medicinal Chemistry Letters 130, pp. 3111-3114, 2003.
Pilling, et al., Inhibition of Fibrocyte Differentiation by Serum Amyloid P., Journal Of Immunology 17, pp. 5537-5546, 2003.
Huang et al., The Monocyte Fcgamma receptors FcgammaRI/gamma and FcgammaRIIA Differ in their Interaction with Syk and with Src-Related Tyrosine Kinases, J. Leukoc Biol 76, pp. 491-499, 2004.
International Search Report with Written Opinion, PCT/US2006/005229, 14 pages, Mailed Oct. 31, 2006.

(Continued)

*Primary Examiner* — Prema Mertz
(74) *Attorney, Agent, or Firm* — Baker Botts L.L.P.

(57) ABSTRACT

The present invention relates to the ability of anti-FcγR antibodies to suppress fibrocytes. Methods and compositions for suppressing fibrocytes are provided. These methods are useful in a variety of applications including treatment and prevention of conditions resulting from fibrosis in the liver, kidney, lung, heart and pericardium, eye, skin, mouth, pancreas, gastrointestinal tract, brain, breast, bone marrow, bone, genitourinary system, a tumor, or a wound.

10 Claims, 6 Drawing Sheets

OTHER PUBLICATIONS

F.C. de Beer et al., "Fibronectin and C4-Binding Protein are Selectively Bound by Aggregated Amyloid Component", The Rockefeller University Press, vol. 154, pp. 1134-1149, Oct. 1981.

Lawrence A. Potempa et al., "Effect of Divalent Metal Ions and pH Upon the Binding Reactivity of Human Serum Amyloid P Component, a C-Reactive Protein Homologue, for Zymosan", The Journal of Biological Chemistry, vol. 260, pp. 12142-12147, Oct. 5, 1985.

Terry W. Du Clos, "C-Reactive Protein Reacts With the U1 Small Nuclear Ribonucleoprotein", The Journal of Immunology, vol. 143, pp. 2553-2559, Oct. 15, 1989.

Marilyn R. Brown et al., "Receptor-Ligand Interactions Between Serum Amyloid P Component and Model Soluble Immune Complexes", The Journal of immunology, vol. 151, pp. 2087-2095, Aug. 15, 1993.

Lorraine L. Marnell et al., "C-Reactive Protein Binds to FcγRI in Transfected COS Cells", The American Association of Immunologists, 9 Pgs, Feb. 22, 1995.

Annalisa D'Andrea et al., "Stimulatory and Inhibitory Effects of Interleukin (IL)-4 and IL-13 on the Production of Cytokines by Human Peripheral Blood Mononuclear Cells: Priming for IL-12 and Tumor Necrosis Factor α Production", The Rockefeller University Press, vol. 181, pp. 537-546, Feb. 1995.

Kamyar Zahedi, "Characterization of the Binding of Serum Amyloid P to Type IV Collagen", The Journal of Biological Chemistry, vol. 271, No. 25, pp. 14897-14902, Jun. 21, 1996.

Marc Daëron, "Fc Receptor Biology", www.arjournals.annualreviews.org, pp. 203-234, 1997.

Kamyar Zahedi, "Characterization of the Binding of Serum Amyloid P to Laminin", The Journal of Biological Chemistry, vol. 272, No. 4, pp. 2143-2148, Jan. 24, 1997.

Carla J.C. de Haas et al., "A Synthetic Lipopolysaccharide-Binding Peptide Based on Amino Acids 27-39 of Serum Amyloid P Component Inhibits Lipopolysaccharide-Induced Responses in Human Blood", The Journal of Immunology, pp. 3607-3615, 1998.

Zheng et al., Piceatannol, a Stilbene Phytochemical, Inhibits Mitochondrial F0F1-ATPase Activity by Targeting the Targeting the F1 Complex, Biochemical And Biophysical Research Communications 261, pp. 499-503, 1999.

Dwaipayan Bharadwaj et al., "The Major Receptor for C-Reactive Protein on Leukocytes Is Fcγ Receptor ll", The Journal of Experimental Medicine, vol. 190 No. 4, pp. 585-590, Aug. 16, 1999.

Su et al., Distinct Mechanisms of STAT Phosphorylation Via the Interferon-Alpha/Beta Receptor, Selective Inhibition of STAT3 and STAT5 by Piceatannol, Journal Of Biological Chemistry 275, pp. 12661-12666, 2000.

Ashikawa et al., Piceatannol Inhibits TNF-Induced NF-KappaB Activation and NF-KappaB-Mediated Gene Expression Through Suppression of IkappaBalpha Kinase and p65 Phosphorylation, J Immunol 169, pp. 6490-6497, 2002.

Charles R.K. Hind et al., "Human Serum Amyloid P Component, a Circulating Lectin with Specificity for the Cyclic 4,6-Pyruvate Acetal of Galactose: Interaction with Varous Bacteria", Biochem.J. 225:107-111, 1985.

Guido Majno, "Chronic Inflammation: Links With Angiogenesis and Wound Healing", American Journal of Pathology, vol. 153, No. 4, pp. 1035-1039, Oct. 1998.

Fayyaz S. Sutterwala et al., "The Taming of IL-12 Suppressing the production of Proinflammatory Cytokines", Journal of Leukocyte Biology, vol. 65, pp. 543-551, May 1999.

M.C.M. Bickerstaff et al., "Serum Amyloid P Component Controls Chromatin Degration and Prevents Antinuclear Autoimmunity", Nature Medicine, vol. 5, No. 6, pp. 694-697, Jun. 1999.

Dwaipayan Bharadwaj et al., "Serum Amyloid P Component Binds to Fcγ Receptors and Opsonizes Particles for Phagocytosis", The Journal of Immunology, vol. 166, pp. 6735-6741, 2001.

Winston L. Hutchinson et al., "Human Serum Amyloid P Component is a Single Uncomplexed Pentamer in Whole Serum", Molecular Medicine, vol. 6, No. 6, pp. 482-493, 2000.

Mary-Pat Stein et al., "C-reactive Protein Binding to FcγRIIa on Human Monocytes and Neutrophils is Allele-Specific", The Journal of Clinical Investigation, vol. 105, pp. 369-376, Feb. 2000.

Richard F. Mortensen et al., "Regulation of Phagocytic Leukocyte Activities by C-reactive Protein", Journal of Leukocyte Biology, vol. 67, pp. 495-500, Apr. 2000.

Carolyn Mold et al., "Serum Amyloid P Component and C-Reactive Protein Mediate Phagocytosis Through Murine FcγRs", The Journal of Immunology, vol. 166, pp. 1200-1205, 2001.

Eirikur Saeland et al., "Human C-reactive Protein Does not Bind to FcγRIIa on Phagocytic Cells", The Journal of Clinical Investigation, vol. 107 No. 5, pp. 641-643, Mar. 2001.

Katherine B. Bodman-Smith et al., "C-Reactive Protein-Mediated Phagocytosis and Phospholipase D Signalling Through the High-Affinity Receptor for Immunoglobulin G (FcγRI)", The Journal of Immunology, vol. 107 No. 2, pp. 252-260, Oct. 2002.

Diana M. Steel et al., "The Major Acute Phase Reactants: C-Reactive Protein, Serum Amyloid P Component and Serum Amyloid A Protein", Immunology Today, vol. 15, No. 2, pp. 81-88, 1994.

Jason Chesney et al., "The Peripheral Blood Fibrocyte is a Potent Antigen-Presenting Cell Capable of Priming Naive T Cells in Situ", Journal of Immunology, vol. 94, pp. 6307-6312, Jun. 1997.

Riichiro Abe et al., "Peripheral Blood Fibrocytes: Differentaion Pathway and Migration to Wound Sites", The Journal of Immunology, vol. 166, pp. 7556-7562, 2001.

John E. Volanakis, "Human C-Reactive Protein: Expression, Structure, and Function", Molecular Immunology, vol. 28, pp. 189-197, 2001.

Liju Yang et al., "Peripheral Blood Fibrocytes From Burn Patients: Identification and Quantification of Fibrocytes in Adherent Cells Cultured From Peripheral Blood Mononuclear Cells", Laboratory Investigation, vol. 82, No. 9, pp. 1183-1192, Apr. 15, 2002.

Darrell Pilling et al., "Inhibition of Fibrocyte Differentation by Serum Amyloid P1", The Journal of Immunology, vol. 171, pp. 5537-5546, 2003.

Thomas A. Wynn, "IL-13 Effector Functions", www.arjournals.annualreviews.org, pp. 425-456, 2003.

C.N. Metz, "Fibrocytes: A unique Cell Population Implicated in Wound Healing", Cell, Mol. Life Sci., vol. 60, pp. 1342-1350, Jan. 16, 2003.

Giorgio Trinchieri, "Interleukin-12 and the Regulation of Innate Resistance and Adaptive Immunity", Nature Reviews Immunology, vol. 3, pp. 133-146, Feb. 2003.

Roderick J. Philips et al., "Circulating Fibrocytes Traffic to the Lungs in Response to CXCL 12 and Mediate Fibrosis", The Journal of Clinical Investigation, vol. 114, No. 3, pp. 438-446, Aug. 2004.

Luca Mori et al., "Fibrocytes Contribute to the Myofibroblast Population in Wounded Skin and Originate From the Bone Marrow", www.sciencedirect.com, pp. 81-90, Aug. 10, 2004.

Liju Yang, PhD et al., "Identification of Fibtocytes in Postburn Hypertrophic Scar", Wound Repair and Regeneration, vol. 13, No. 4, pp. 398-404, Jan. 17, 2005.

M.B. Pepys et al., "Serum Amyloid P Component is the Major Calcium-Dependent Specific DNA Binding Protein of Serum", Biochemical and Biophysical Research Communications, vol. 148, No. 1, pp. 208-313, Oct. 14, 1987.

R.B. Christner et al., "Binding of Human Serum Amyloid P-Component to Phosphocholine", Archives of Biochemistry and Biophysics, vol. 314, No. 2, pp. 337-343, Nov. 1, 1994.

R. Bucala et al., "Circulating Fibrocytes Define a New Leukocyte Subpopulation That Mediates Tissue Repair", Molecular Medicine, vol. 1, No. 1, pp. 71-81, Nov. 1994.

M.B. Pepys et al., "Amyloid P Component. A Critical Review", Amyloid: Int. J. Exp. Invest., vol. 4, pp. 274-295, 1997.

J. Chesney et al., "Regulated Production of Type I Collagen and Inflammatory Cytokins by Peripheral Blood Fibrocytes", The Journal of Immunology, pp. 15, 1998.

J. Chesney et al., "Peripheral Blood Fibrocytes: Mesenchymal Precursor Cells and the Pathogenesis of Fibrosis", Curr.Rheumatol.Rep 2:501-505, 2000.

Richard A.F. Clark, "Fibrin and Wound Healing", Annals New York Academy of Sciences 936, pp. 355-367, 2001.

M. Chi et al., "C-Reactive Protein Induces Signaling Through FcγRIIa on HL-60 Granulocytes", The Journal of Immunology, pp. 1413-1418, 2002.

F.C. De Beer et al., "Isolation of Human C-Reactive Protein and serum Amyloid P Component", Journal of Immunological Methods, pp. 17-31, 1982.

H. Gewurz et al., "Structure and Function of the Pentraxins", Current Opinion in Immunology, vol. 7, pp. 54-64, 1995.

Niels H.H. Heegaard et al., "Ligand-Binding Sites in Human Serum Amyloid P Component", Eur.J.Biochem. 239:850-856, 1996.

Marc Daëon, "Structural Bases of FcγR Functions", Int.Rev.Immunol. 16:1-27, 1997.

E. Saeland et al., "Human C-Reactive Protein Does not Bind to FcγRIIa on Phagocytic Cells", The Journal of Clinical Investigation, vol. 107, No. 5, pp. 641-643, Mar. 2001.

Ingo Hartiapp et al., "Fibrocytes Induce an Angiogenic Phenotype in Cultured Endothelial Cells and Promote Angiogenesis in Vivo", The FASEB Journal, vol. 15, pp. 2215-2224, Oct. 2001.

M.G. Cappiello et al., "Suppression of IL-12 Transcription in Macrophages Following Fcγ Receptor Ligation", The Journal of Immunology, vol. 166, pp. 4498-4506, 2001.

Matthias Schmidt et al., "Identification of Circulating Fibrocytes as Precursors of Bronchial Myofibroblasts in Asthma", The Journal of Immunology, vol. 170, pp. 380-389, Apr. 22, 2003.

Bethany B. Moore et al., "CCR2-Mediated Recruitment of Fibrocytes to the Alveolar Space After Fibrotic Injury", American journal of Pathology, vol. 166, No. 3, pp. 675-684, Mar. 2005.

Ashcroft et al., "Simple Method of Estimating Severity of Pulmonary Fibrosis on a Numerical Scale", J Clin Pathol 41, pp. 467-470, 1988.

Brown, "The role of extracellular matrix proteins in the control of phagocytosis", Journal of Leukocyte Biology, vol. 39, (pp. 579-591), 1986.

Crouch, E., "Patholbiology of Pulmonary Fibrosis", Am J Physiol Lung Cell Mol Physiol 259, pp. L159-L184, 1990.

De Beer et al., "Isolation and Characterization of C-Reactive Protein and Serum Amyloid P Component in the Rat", Immunology 45, pp. 55-70, 1982.

Du Clos, et al., "Reply to Human C-reactive protein does not bind to fc gamma RIIa on phagocytic cells", The Journal of Clinical Investigation, vol. 107, No. 5, pp. 643, 2001.

Emsley et al., "Structure of Pentameric Human Serum Amyloid P Component", Nature 367, pp. 338-345, 1994.

Grazia, et al., "Suppression of IL-12 Transcription in Macrophages Following Fc Receptor Ligation", The Journal of Immunology, vol. 166, (pp. 4498-4506), 2001.

Gregory et al., "The DNA Sequence and Biological Annotation of Human Chromosome 1", Nature 441, pp. 315, 2006.

Harris et al., "Pegylation A Novel Process for Modifying Pharmacokinetics", Clin. Pharmacokinetic 2001, vol. 40, No. 7 (pp. 539-551), 2001.

Hohenester et al., "Crystal Structure of a Decameric Complex of Human Serum Amyloid P Component with Bound dAMP", J. Mol. Biol. 269, pp. 570-578, 1997.

International Search Report OR (Examination Report) for European Patent Application No. 03 800 146.7 (5 pages), 2007.

Kisseleva et al., Bone Marrow-Derived Fibrocytes Participate in Pathogenesis of Liver Fibrosis, 45 Journal of Hepatology, pp. 429-438, 2006.

Lei et al., "Genomic DNA Sequence for Human C-Reactive Protein", J. Biol. Chem. 260, pp. 13377-13383, 1985.

Lindenbaum et al., "Serum-Free Cell Culture Medium Induces Acceleration of Wound Healing in Guinea-Pigs", Burns, vol. 21, No. 2 (pp. 110-115), 1995.

Liu et al., "Human Plasma N-Glycoproteome Analysis by Immunoaffinity Subtraction, Hydrazide Chemistry, and Mass Spectrometry", J. Proteome Res. 4, pp. 2070-2080, 2005.

Mantzouranis et al., "Human Serum Amyloid P Component", cDNA Isolation, Complete Sequence of Pre-Serum Amyloid P Component, and Localization of the Gene to Chromosome 1, The Journal of Biological Chemistry, vol. 260, No. 12, pp. 7752-7756, 1985.

Murphy et al., "Extrahepetic Transcription of Human C-Reactive Protein", Journal of Experimental Medicine, vol. 73, (pp. 495-498), 1991.

Ohnishi et al., "Isolation and Characterization of the Complete Complementary and Genomic DNA Sequences of Human Serum Amyloid P Component", J. Biochem. 100, pp. 849-858, 1986.

Oliveira et al., "Primary Structure of Human C-Reactive Protein", The Journal of Biological Chemistry, vol. 254, No. 2, (pp. 489-502), 1979.

Oriente et al., "Interleukin-13 Modulates Collagen Homeostasis in Human Skin and Keloid Fibroblasts", The Journal of Pharmacology and Experimental Therapeutics, vol. 292, No. 3 (pp. 988-994), 2000.

Osmand et al., Partial Amino-Acid Sequences of Human and Rabbit C-Reactive Proteins: Homology with Immunoglobulins and Histocompatibility AntigensProc. Natl. Acad. Sci. U.S.A. vol. 74, No. 3, (pp. 1214-1218), 1977.

Pachence, et al., "Tissue-Activated Delivery—Novel Methods for Site-Directed Drug Delivery", Drug Delivery Technology, vol. 3, No. 1, (pp. 40-45.), 2003.

Pepys et al., "Human Serum Amyloid P Component is an Invariant Constituent of Amyloid Deposits and has a Uniquely Homogeneous Glycostructure", Proc. Natl. Acad. Sci. U.S.A., vol. 91, (pp. 5602-5606), 1994.

Pontet, et al., "One step preparation of both human C-reactive protein and CIt", FEBS Letters, vol. 88, No. 2, pp. 172-175, 1978.

Prelli et al., "The Primary Structure of Human Tissue Amyloid P Component From A Patient with Primary Idiopathic Amyloidosis", The Journal of Biological Chemistry, vol. 260, No. 24, (pp. 12895-12898), 1985.

Russo et al., "Liver Fibrosis; Bone Marrow Functionality Contributes to Liver Fibrosis", 130(6) Gastroenterology Week Jul. 31, 2006, (pp. 83-84), 2006.

Shrive et al., "Three Dimensional Structure of Human C-Reactive Protein", Nature Structural Biology, vol. 3, No. 4, (pp. 346-353), 1996.

Sjoeblom et al., "The Consensus Coding Sequences of Human Breast and Colorectal Cancers", Science vol. 314, www.sciencemag.org, (pp. 268-274), 2006.

Srinivasan et al., "Comparative Analyses of Pentraxins: Implications for Protomer Assembly and Ligand Binding", Structure, vol. 2, No. 11, (pp. 1017-1027), 1994.

The MGC Project Team, "The Status, Quality, and Expansion of the NIH Full-Length cDNA Project: The Mammalian Gene Collection (MGC)", Genome Research, 14, pp. 2121-2127, 2004.

Thompson et al., "Human Plasma P Component: Isolation and Characterization", Biochemistry, vol. 17, No. 20, (pp. 4304-4311), 1978.

Thompson et al., "The Physiological Structure of Human C-Reactive Protein and its Complex with Phosphocholine", Structure, vol. 7, No. 2, (pp. 169-177), 1999.

Tucci et al., "Biosynthesis and Postsynthetic Processing of Human C-Reactive Protein", The Journal of Immunology, vol. 131, No. 5, pp. 2416-2419, 1983.

Turner et al., "Tyrosine Kinase SYK: Essential Functions for Immunoreceptor Signalling", Review Immunology Today, vol. 21, No. 3 (pp. 148-154), 2000.

Underwood et al., SB 239063, "A p38 MAPK Inhibitor, reduces Neutrophilia, Infamatory Cytokines, MMP-9, and Fibrosis in Lung", Am J Physiol Lung Cell Mol Physiol, vol. 279, pp. L895-L902, 2000.

Vidal et al., "Inducible expression of PTX3, a new member of the pentraxin family, in human mononuclear phagocytes", Blood, vol. 84, No. 10, (pp. 3483-3493), 1994.

Whitehead et al., "Isolation of Human C-Reactive Protein Complementary DNA and Localization of the Gene to Chromosome 1", Science, vol. 221, No. 4605, pp. 69-71. http://www.jstor.org/stable/1691455, 1983.

Woo et al., "Characterization of Genomic and Complementary DNA Sequence of Human C-Reactive Protein, and Comparison with the Complementary DNA Sequence of Serum Amyloid P Component", The Journal of Biological Chemistry, vol. 260, No. 24, (pp. 13384-13388), 1985.

Zheng et al., "Piceatannol, a Stilbene Phytochemical, Inhibits Mitochondrial F0F1-ATPase Activity by Targeting the F1 Complex", Biochemical and Biophysical Research Communications, vol. 261, No. 2, (pp. 499-503), 1999.

International Search Report, PCT/US2003/041183, 5 pages, 2004.
International Search Report, PCT/US2003/040957, 7 pages, 2004.

Junqueira et al., "Picrosirius Straining Plus Polarization Microscopy, A Specific Method for Collagen Detection in Tissue Sections", Histochem. J 11, pp. 447-455, 1979.

Kiernan et al., "Proteomic Characterization of Novel Serum Amyloid P Component Variants from Human Plasma and Urine", Proteomics 4, (pp. 1825-1829), 2004.

European Office Action; Application No. 03 814 319.4-2404; pp. 8, Apr. 21, 2009.

Australian Office Action; Application No. 2003299873; pp. 2, Apr. 23, 2009.

Japanese Office Action; Application No. 2004-564024 dated Jul. 7, 2010; pp. 3, Jul. 7, 2010.

Hind et al.; "Binding Specificity of Serum Amyloid P Component for the Pyruvate Acetal of Galactose"; J. Exp. Med., vol. 159; pp. 1058-1069, Apr. 1984.

Duckworth et al.; "The Structure of Agar Part 1. Fractionation of a Complex Mixture of Polysaccharides"; Carbohydrate Research, vol. 16; pp. 189-197, 1971.

Young et al.; "The Structure of Agar Part III*. Pyruvic Acid, a Common Feature of Agars From Different Agarophytes"; Carbohydrate Research, vol. 16; pp. 446-448, 1971.

Schwalbe et al.; "Pentraxin Family of Proteins Interact Specifically with Phosphorylcholine and/or Phosporylethanolamine"; Biochemistry, vol. 31; pp. 4907-4615, 1992.

Weimann et al.; "Studies of Wound Healing: Effects of Calcium D-Panthothenate on the Migration, Proliferation and Protein Synthesis of Human Dermal Fibroblasts in Culture"; Internat. J. Vit. Nutr. Res., 69(2); pp. 113-119, 1999.

Gehring et al.; "Effect of Topically Applied Dexpanthenol on Epidermal Barrier Function and Stratum Corneum Hydration"; Arzneim.-Forsch./Drug Res.; 50(11); pp. 7, 2000.

Ishaque et al.; "Role of Vitamins in Determining Apoptosis and Extent of Suppression by bcl-2 During hybridoma Cell Culture"; Apoptosis; vol. 7, No. 3; pp. 231-239, 2002.

R.H. Painter; "Evidence that C1t (amyloid P-component) is not a subcomponent of the first component of complement (C1)"; J. Immunol.; 119(6); pp. 2203-2205, 1977.

M.B. Pepys; "Isolation of serum amyloid P-component (protein SAP) in the mouse"; Immunology; 37(3); pp. 637-641, 1977.

C.R. Hind et al.; "Binding specificity of serum amyloid P-component for the pyruvate acetal of galactose"; Journal of Experimental Medicine; 159(4); pp. 1058, 1984.

COMPOSITIONS AND METHODS FOR SUPPRESSING FIBROCYTES

PRIORITY CLAIM

The present application is a continuation-in-part under 35 U.S.C. §120 of PCT patent application serial number PCT/US2006/005229, filed Feb. 15, 2006 and titled "Methods and Conditions for Suppressing Fibrocyte Differentiation" and Ser. No. 11/158,966, now U.S. Pat. No. 7,666,432 U.S. Application No. 2005/0238620 filed Jun. 22, 2005, which is a continuation-in-part under 35 U.S.C. §120 of PCT patent application serial number PCT/US2003/040957, filed Dec. 22, 2003 and titled "Methods and Conditions for Suppressing Fibrocyte Differentiation", published in English as WO 2004/058292 on Jul. 15, 2004; which claims priority to the following: U.S. Provisional Patent Applications 60/436,046, filed Dec. 23, 2002; U.S. 60/436,027, filed Dec. 23, 2002; U.S. 60/515,776, filed Oct. 30, 2003; U.S. 60/519,467, filed Nov. 12, 2003; and U.S. 60/525,175 filed Nov. 26, 2003. Pertinent parts of the application are incorporated by reference herein.

FIELD OF THE INVENTION

The present invention relates to the ability of anti-FcγR antibodies, aggregated IgG, and/or cross-linked IgG to suppress fibrocytes. Accordingly, it may include compositions and methods for suppressing fibrocytes. These compositions and methods may be useful in a variety of applications, for example, those in which decreased fibrocyte formation is beneficial, such as treatment of fibrosing diseases and asthma.

BACKGROUND

Fibrocytes

Inflammation is the coordinated response to tissue injury or infection. The initiating events are mediated by local release of chemotactic factors, platelet activation, and initiations of the coagulation and complement pathways. These events stimulate the local endothelium, promoting the extravasation of neutrophils and monocytes. The second phase of inflammation is characterized by the influx into the tissue of cells of the adaptive immune system, including lymphocytes. The subsequent resolution phase, when apoptosis of the excess leukocytes and engulfment by tissue macrophages takes place, is also characterized by repair of tissue damage by stromal cells, such as fibroblasts.

In chronic inflammation, the resolution of inflammatory lesions is disordered, with the maintenance of inflammatory cells, fibroblast hyperplasia, and eventual tissue destruction. The mechanisms that lead to these events are complex, but include enhanced recruitment, survival and retention of cells and impaired emigration.

The source of fibroblasts responsible for repair of wound lesions or in other fibrotic responses is controversial. The conventional hypothesis suggests that local quiescent fibroblasts migrate into the affected area, produce extracellular matrix proteins, and promote wound contraction or fibrosis. An alternative hypothesis is that circulating fibroblast precursors (called fibrocytes) present within the blood migrate to the sites of injury or fibrosis, where they differentiate and mediate tissue repair and other fibrotic responses.

Fibrocytes are fibroblast-like cells that appear to participate in wound healing and are present in pathological lesions associated with, inter alia, asthma, pulmonary fibrosis and scleroderma. Fibrocytes are known to differentiate from a CD14+ peripheral blood monocyte precursor population. Fibrocytes may also differentiate from other sources. Fibrocytes express markers of both hematopoietic cells (CD45, MHC class II, CD34) and stromal cells (collagen types I and III and fibronectin). Fibrocytes at sites of tissue injury secrete inflammatory cytokines, extracellular matrix proteins and promote angiogenesis and wound contraction. Fibrocytes are also associated with the formation of fibrotic lesions after infection or inflammation, and are implicated in fibrosis associated with autoimmune diseases.

Control of fibrocyte differentiation is likely to be important in the control of many diseases and processes. Fibrocytes are associated with a variety of processes and diseases including scleroderma, keloid scarring, rheumatoid arthritis, lupus, nephrogenic fibrosing dermopathy, and idiopathic pulmonary fibrosis. They play a role in the formation of fibrotic lesions after *Schistosoma japonicum* infection in mice and are also implicated in fibrosis associated with autoimmune diseases. Fibrocytes have also been implicated in pathogenic fibrosis, fibrosis associated with radiation damage, Lyme disease and pulmonary fibrosis. CD34+ fibrocytes have also been associated with stromal remodeling in pancreatitis and stromal fibrosis, whereas lack of such fibrocytes is associated with pancreatic tumors and adenocarcinomas. Fibrosis additionally occurs in asthma patients and possibly other pulmonary diseases such as chronic obstructive pulmonary disease when fibrocytes undergo further differentiation into myofibroblasts.

Fibrocytes may also play a role in a variety of conditions, likely even some in which fibrocyte formation is not currently known. Some additional conditions may include congestive heart failure, other post-ischemic conditions, post-surgical scarring including abdominal adhesions, corneal refraction surgery, and wide angle glaucoma trabeculectomy. Fibrocytes are also implicated in liver fibrosis and cirrhosis. See Tatiana Kisseleva et al, *Bone Marrow-Derived Fibrocytes Participate in Pathogenesis of Liver Fibrosis*, 45 Journal of Hepatology 429-438 (September 2006); see also F. P. Russo et al, *The Bone Marrow Functionality Contributes to Liver Fibrosis*, 130(6) Gastroenterology 1807-21 (May 2006). Fibrocytes are important in the formation of tumors, particularly stromal tissue in tumors. Recent evidence also suggests that fibrocytes may further differentiate into adipocytes and thus play a role in obesity.

It has been previously identified that fibrocytes may differentiate from CD14+ peripheral blood monocytes, and the presence of human serum dramatically delays this process. The factor in human serum that inhibits fibrocyte differentiation is serum amyloid P (SAP). SAP, a member of the pentraxin family of proteins that includes C-reactive protein (CRP), is produced by the liver, secreted into the blood, and circulates in the blood as stable pentamers. SAP binds to receptors for the Fc portion of IgG antibodies (FcγR) on a variety of cells and may effectively cross-link FcγR without additional proteins because SAP is a pentameric protein with five potential FcγR binding sites per molecule. As SAP binds to FcγR, intracellular signaling events consistent with FcγR activation are initiated.

Anti-FcγR Antibodies

It has also been identified that anti-FcγR antibodies may also prevent the differentiation of peripheral blood monocytes into fibrocytes. Anti-FcγR antibodies are IgG antibodies that bind to receptors for the Fc portion of IgG antibodies (FcγR). The anti-FcγR antibodies bind through their variable region, and not through their constant (Fc) region. However, IgG from the appropriate source (e.g. human IgG for human receptors) may normally bind to FcγR through its Fc region. FcγR are found on the surface of a variety of hematopoietic cells. There are four distinct classes of FcγR. FcγRI (CD64) is expressed by peripheral blood monocytes and binds monomeric IgG with a high affinity. FcγRII (CD32) and FcγRIII (CD16) are low affinity receptors for IgG and only efficiently bind aggregated IgG. FcγRII is expressed by peripheral blood B cells and monocytes, whereas FcγRIII is expressed by NK cells and a subpopulation of monocytes. FcγRIV was recently identified in mice and is present on murine peripheral blood monocytes and neutrophils, macrophages and dendritic cells and efficiently binds murine IgG2a and IgG2b antibodies. There is a putative human FcγRIV gene, but the biological function of the protein, such as ligand specificity and cellular expression is, as yet unknown.

Peripheral blood monocytes express both FcγRI and FcγRII (a subpopulation of monocytes express FcγRIII), whereas tissue macrophages express all three classical FcγR. Clustering of FcγR on monocytes by IgG, either bound to pathogens or as part of an immune complex, initiates a wide variety of biochemical events.

FcγR activation and induction of intracellular signaling pathways may occur when multiple FcγR are cross-linked or aggregated. This FcγR activation leads to a cascade of signaling events initiated by two main kinases. The initial events following FcγR activation involve the phosphorylation of intracellular immunoreceptor tyrosine activation motifs (ITAMs) present on the cytoplasmic tail of FcγRIIa or the FcR-γ chain associated with FcγRI and FcγRIII, by Src-related tyrosine kinases (SRTK). In monocytes, the main Src-kinases associated with FcγRI and FcγRII are hck and lyn. The phosphorylated ITAM then recruit cytoplasmic SH2-containing kinases, especially Syk, to the ITAMs and Syk then activates a series of downstream signaling molecules.

Anti-FcγR antibodies for FcγRI (anti-FcγRI) and for FcγRII (anti-FcγRII) are able to bind to either FcγRI or FcγRII, respectively. These FcγR may then be cross-linked by the binding of additional antibodies or other means. This process initiates intracellular signaling events consistent with FcγR activation.

Scleroderma

Scleroderma is a non-inherited, noninfectious disease that has a range of symptoms. It involves the formation of scar tissue containing fibroblasts in the skin and internal organs. The origin of the fibroblasts is unknown. In mild or early cases of scleroderma, there is a hardening of the skin, fatigue, aches and sensitivity to cold. In more severe and later stages, there is high blood pressure, skin ulcers, difficulty moving joints, and death from lung scarring or kidney failure. Approximately 300,000 people in the U.S. have scleroderma. The disease has similarities to lupus and rheumatoid arthritis. There is no cure or significant treatment for scleroderma and even diagnosis is difficult because there is no clinical test.

Nephrogenic Fibrosing Dermopathy

Nephrogenic fibrosing dermopathy (NFD) is a newly recognized scleroderma-like fibrosing skin condition. It develops in patients with renal insufficiency. Yellow scleral plaques and circulating antiphospholipid antibodies have been proposed as markers of NFD. Dual immunohistochemical staining for CD34 and pro-collagen in the spindle cells of NFD suggest that the dermal cells of NFD may represent circulating fibrocytes recruited to the dermis. Therefore, inhibition of fibrocyte formation may alleviate symptoms of this disease.

Asthma

Asthma affects more than 100 million people worldwide, and its prevalence is increasing. Asthma appears to be caused by chronic airway inflammation. One of the most destructive aspects of asthma is remodeling of the airways in response to chronic inflammation. This remodeling involves thickening of the lamina reticularis (the subepithelial reticular basement membrane surrounding airways) due to fibrosis. The airway passages then become constricted due to the thickened airway walls.

The thickened lamina reticularis in asthma patients contains abnormally high levels of extracellular matrix proteins such as collagen I, collagen III, collagen V, fibronectin and tenascin. The source of these proteins appears to be a specialized type of fibroblast called myofibroblasts.

In asthma patients, CD34+/collagen I+ fibrocytes accumulate near the basement membrane of the bronchial mucosa within 4 hours of allergen exposure. 24 hours after allergen exposure, labeled monocytes/fibrocytes have been observed to express α-smooth muscle actin, a marker for myofibroblasts. These observations suggest that in asthma patients allergen exposure causes fibrocytes from the blood to enter the bronchial mucosa, differentiate into myofibroblasts, and then cause airway wall thickening and obstruct the airways. Further, there is a correlation between having a mutation in the regulatory regions of the genes encoding monocyte chemoattractant protein 1 or TGFβ-1 and the severity of asthma. This also suggests that recruitment of monocytes and appearance of myofibroblasts lead to complications of asthma.

Thickening of the lamina reticularis distinguishes asthma from chronic bronchitis or chronic obstructive pulmonary disease and is found even when asthma is controlled with conventional medications. An increased extent of airway wall thickening is associated with severe asthma. No medications or treatments have been found to reduce thickening of the lamina reticularis. However, it appears likely that reducing the number of myofibroblasts found in the airway walls may reduce thickening or help prevent further thickening.

Idiopathic Pulmonary Fibrosis

Idiopathic pulmonary fibrosis (IPF) is a unique type of chronic fibrosing lung disease of unknown etiology. The sequence of the pathogenic mechanisms is unknown, but the disease is characterized by epithelial injury and activation, the formation of distinctive subepithelial fibroblast/myofibroblast foci, and excessive extracellular matrix accumulation. These pathological processes usually lead to progressive and irreversible changes in the lung architecture, resulting in progressive respiratory insufficiency and an almost universally terminal outcome in a relatively short period of time. While research has largely focused on inflammatory mechanisms for initiating the fibrotic response, recent evidence strongly suggests that disruption of the alveolar epithelium is an underlying pathogenic event. Given the role played by fibrocytes in wound healing and their known role in airway wall thickening in asthma, it appears likely that overproduction of fibrocytes may be implicated in IPF.

SUMMARY

The present invention may include compositions and methods for suppressing fibrocytes. In the context of the present invention, the term "suppressing fibrocytes" refers to one or more of inhibiting the proliferation of fibrocytes, inhibiting the development of fibrocytes, including the development or differentiation of a cell into a fibrocyte, and promoting the development or differentiation of fibrocytes into non-fibrocytic cell types.

In selected embodiments, fibrocytes may be suppressed in a target location by providing anti-FcγR antibodies that are able to cross-link FcγR. The target location may be located in vitro or in vivo. Specifically, the target location may be located in a mammal, such as a human patient.

In vivo, the target location may include an entire organism or a portion thereof and the composition may be administered systemically or it may be confined to a particular area, such as an organ or tissue.

Suppressing fibrocytes may alleviate symptoms of numerous fibrosing diseases or other disorders caused by fibrosis. In a specific embodiment, administration of anti-FcγR antibodies may be used to treat the effects of unwanted fibrocytes. For example, it may be used to treat fibrosis in the liver, kidney, lung, heart and pericardium, eye, skin, mouth, pancreas, gastrointestinal tract, brain, breast, bone marrow, bone, genitourinary, a tumor, or a wound.

BRIEF DESCRIPTION OF THE DRAWINGS

The following figures form part of the present specification and are included to further demonstrate certain aspects of the present invention.

FIG. 4 shows the effects of cross-linking IgG and other antibody isotypes and on fibrocyte differentiation.

FIG. 6 shows the effects of ligation and cross-linking of Fc receptors on monocyte to fibrocyte differentiation. Soluble immune complexes (ovalbumin-antibody), particulate immune complexes, including opsonised sheep red blood cells (SRBC) and heat-aggregated IgG were used.

DETAILED DESCRIPTION

Figure 1:
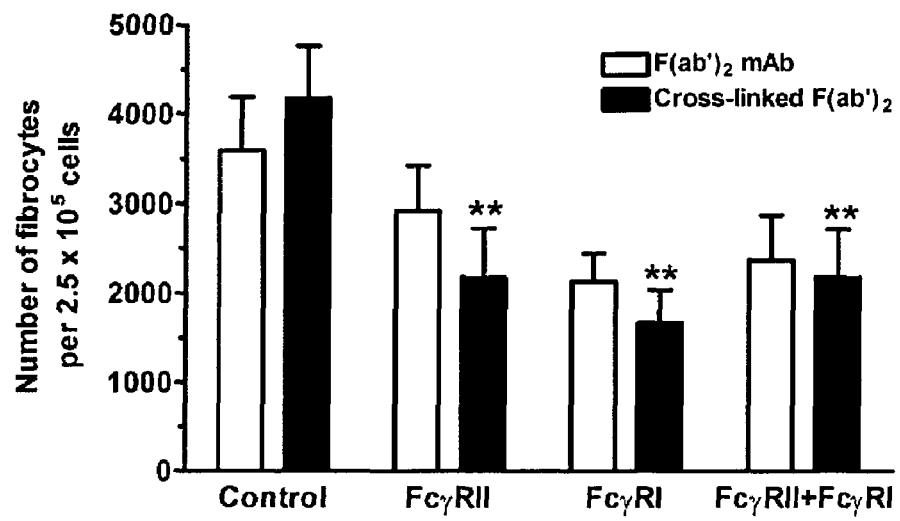
FIG. 1 shows the effects of cross-linked and non-cross-linked anti-FcγR antibodies on fibrocyte differentiation from Peripheral Blood Mononuclear Cells (PBMC). PBMC at $2.5\times10^5$ cells per ml were cultured in serum-free medium for 5 days in the presence or absence of 1 µg/ml of the indicated $F(ab')_2$ anti-FcγR or control IgG1 antibodies, in the presence (black bars) or absence (white bars) of 500 ng/ml goat $F(ab')_2$ anti-mouse IgG, which cross-links the $F(ab')_2$. Cells were then air-dried, fixed, stained, and fibrocytes were enumerated by morphology.

The regulation of events leading to fibrosis involves the proliferation and differentiation of fibrocytes. Fibrocytes are a distinct population of fibroblast-like cells derived from peripheral blood monocytes that normally enter sites of tissue injury to promote angiogenesis and wound healing. Fibrocytes differentiate from CD14+ peripheral blood monocytes, and may differentiate from other PBMC cells. The presence of anti-FcγR antibodies, aggregated IgG, and/or cross-linked IgG may inhibit or at least partially delay this process.

Compositions containing anti-FcγRI antibodies and/or anti-FcγRII antibodies, and/or cross-linked or aggregated IgG, which may bind to FcγR through the Fc region, may be used to suppress fibrosis in inappropriate locations and in fibrosing disorders and chronic inflammatory conditions, inter alia.

In specific embodiments, compositions containing approximately 1 µg/ml anti-FcγR antibodies may be effective to inhibit fibrocyte proliferation or differentiation by approximately 50%. In other embodiments, compositions may contain an amount sufficient to deliver 1 µg/ml anti-FcγR antibodies to a target location (e.g., a tissue). In other specific embodiments, compositions may contain as little as 0.1 µg ml cross-linked or aggregated IgG.

Anti-FcγR antibodies may be administered in a dose of approximately 1.0 µg/mL, in an amount sufficient to deliver 1 µg/ml anti-FcγR antibodies to the target tissue, or in another dose sufficient to inhibit fibrocyte proliferation or differentiation without causing an undesirable amount of cell death in the patient. Aggregated or cross-linked IgG may be administered in an amount sufficient to deliver at least 0.1 µg/ml IgG to the target location, or in another dose sufficient to suppress fibrocytes without causing an undesirable amount of cell death in the patient.

Anti-FcγR antibodies used in examples of the present disclosure include anti-FcγRI antibodies and anti-FcγRII antibodies. Cross-linked or aggregated IgG may include any IgG able to bind the target FcγR through its Fc region, provided that at least two such IgG antibodies are physically connected to one another.

Antibodies of both types may include whole antibodies or a portion thereof, preferably the portion functional in suppressing fibrocytes. For example, they may include any antibody portion able to cross-link FcγR. This may include aggregated or cross-linked antibodies or fragments thereof, such as aggregated or cross-linked whole antibodies, F(ab')$_2$ fragments, and possibly even Fc fragments.

Aggregation or cross-linking of antibodies may be accomplished by any known method, such as heat or chemical aggregation. Any level of aggregation or cross-linking may be sufficient, although increased aggregation may result in increased fibrocyte suppression. Antibodies may be polyclonal or monoclonal, such as antibodies produced from hybridoma cells. Compositions and methods may employ mixtures of antibodies, such as mixtures of multiple monoclonal antibodies, which may be cross-linked or aggregated to like or different antibodies.

Anti-FcγR antibodies may include any isotype of antibody.

Compositions may be applied locally or systemically. The compositions may also be supplied in combinations or with cofactors. Compositions may be administered in an amount sufficient to restore normal levels, if the composition is normally present in the target location, or they may be administered in an amount to raise levels above normal levels in the target location.

The compositions of the present invention may be supplied to a target location from an exogenous source, or they may be made in vivo by cells in the target location or cells in the same organism as the target location.

Compositions of the present invention may be in any physiologically appropriate formulation. They may be administered to an organism by injection, topically, by inhalation, orally or by any other effective means.

The same compositions and methodologies described above to suppress fibrocytes may also be used to treat or prevent conditions resulting from inappropriate fibrocyte proliferation or differentiation. For example, they may treat or prevent a condition occurring in the liver, kidney, lung, heart and pericardium, eye, skin, mouth, pancreas, gastrointestinal tract, brain, breast, bone marrow, bone, genitourinary, a tumor, or a wound.

Generally, they may treat or prevent fibrosis resulting from conditions including but not limited to rheumatoid arthritis, lupus, pathogenic fibrosis, fibrosing disease, fibrotic lesions such as those formed after *Schistosoma japonicum* infection, radiation damage, autoimmune diseases, Lyme disease, chemotherapy induced fibrosis, HIV or infection-induced focal sclerosis, failed back syndrome due to spinal surgery scarring, abdominal adhesion post surgery scarring, fibrocystic formations, fibrosis after spinal injury, surgery-induced fibrosis, mucosal fibrosis, peritoneal fibrosis caused by dialysis, and Adalimumab-associated pulmonary fibrosis.

Specifically, in the liver, they may treat or prevent fibrosis resulting from conditions including but not limited to alcohol, drug, and/or chemically induced cirrhosis, ischemia-reperfusion injury after hepatic transplant, necrotizing hepatitis, hepatitis B, hepatitis C, primary biliary cirrhosis, and primary sclerosing cholangitis.

Relating to the kidney, they may treat or prevent fibrosis resulting from conditions including but not limited to proliferative and sclerosing glomerulonephritis, nephrogenic fibrosing dermopathy, diabetic nephropathy, renal tubulointerstitial fibrosis, and focal segmental glomerulosclerosis.

Relating to the lung, they may treat or prevent fibrosis resulting from conditions including but not limited to pulmonary interstitial fibrosis, sarcoidosis, pulmonary fibrosis, idiopathic pulmonary fibrosis, asthma, chronic obstructive pulmonary disease, diffuse alveolar damage disease, pulmonary hypertension, neonatal bronchopulmonary dysplasia, chronic asthma, and emphysema. There are several subnames or synonyms for pulmonary fibrosis including, but not limited to, cryptogenic fibrosing alveolitis, diffuse interstitial fibrosis, idiopathic interstitial pneumonitis, Hamman-Rich syndrome, silicosis, asbestosis, berylliosis, coal worker's pneumoconiosis, black lung disease, coal miner's disease, miner's asthma, anthracosis, and anthracosilicosis.

Relating to the heart and/or pericardium, they may treat or prevent fibrosis resulting from conditions including but not limited to myocardial fibrosis, atherosclerosis, coronary artery restenosis, congestive cardiomyopathy, heart failure, and other post-ischemic conditions.

Relating to the eye, they may treat or prevent fibrosis resulting from conditions including but not limited to exophthalmos of Grave's disease, proliferative vitreoretinopathy, anterior capsule cataract, corneal fibrosis, corneal scarring due to surgery, trabeculectomy-induced fibrosis, progressive subretinal fibrosis, multifocal granulomatous chorioretinitis, and other eye fibrosis.

Relating to the skin, they may treat or prevent fibrosis resulting from conditions including but not limited to Depuytren's contracture, scleroderma, keloid scarring, psoriasis, hypertrophic scarring due to burns, atherosclerosis, restenosis, and psuedoscleroderma caused by spinal cord injury.

Relating to the mouth and/or esophagus, they may treat or prevent fibrosis resulting from conditions including but not limited to periodontal disease scarring, gingival hypertrophy secondary to drugs, and congenital esophageal stenosis.

Relating to the pancreas, they may treat or prevent fibrosis resulting from conditions including but not limited to pancreatic fibrosis, stromal remodeling pancreatitis, and stromal fibrosis.

Relating to the gastrointestinal tract, they may treat or prevent fibrosis resulting from conditions including but not limited to collagenous colitis, villous atrophy, cryp hyperplasia, polyp formation, fibrosis of Crohn's disease, and healing gastric ulcer.

Relating to the brain, they may treat or prevent fibrosis resulting from conditions including but not limited to glial scar tissue.

Relating to the breast, they may treat or prevent fibrosis resulting from conditions including but not limited to fibrocystic disease and desmoplastic reaction to breast cancer.

Relating to the bone marrow, they may treat or prevent fibrosis resulting from conditions including but not limited to fibrosis in myelodysplasia and neoplastic diseases.

Relating to the bone, they may treat or prevent fibrosis resulting from conditions including but not limited to rheumatoid pannus formation.

Relating to the genitourinary system, they may treat or prevent fibrosis resulting from conditions including but not limited to endometriosis, uterine fibroids, ovarian fibroids, and Peyronie's disease.

Relating to radiation induced damage, they may treat or prevent fibrosis related to, but not limited to, treatment of head and neck cancer, ovarian cancer, prostate cancer, lung cancer, gastrointestinal cancer, colon cancer, and breast cancer.

The following examples are included to demonstrate specific embodiments of the invention. It should be appreciated by those of skill in the art that the techniques disclosed in the examples that follow represent techniques discovered by the inventors to function well in the practice of the invention. However, those of skill in the art should, in light of the present disclosure, appreciate that many changes can be made in the specific embodiments that are disclosed and still obtain a like or similar result without departing from the spirit and scope of the invention.

EXAMPLES

Example 1

Fibrocyte Differentiation Assay

Human peripheral blood mononuclear cells (PBMC) were isolated from buffy coats (Gulf Coast Regional Blood Center, Houston, Tex.) by Ficoll-Paque Plus (Amersham Biosciences, Piscataway, N.J.). Cells were incubated in serum-free medium (SFM), which consists of RPMI (Invitrogen, Carlsbad, Calif.) supplemented with 10 mM HEPES (Invitrogen), 2 mM glutamine, 100 U/ml penicillin, 100 µg/ml streptomycin, and 1×ITS-3 (500 µg/ml bovine serum albumin, 10 µg/ml insulin, 5 µg/ml transferrin, 5 ng/ml sodium selenite, 5 µg/ml linoleic acid, and 5 µg/ml oleic acid; Sigma-Aldrich, St. Louis, Mo.). Normal human serum (Sigma-Aldrich) was added at 1%. PBMC were cultured in flat-bottomed 96 well tissue culture plates (Type 353072, BD Biosciences Discovery Labware, Bedford, Mass.) in 200 µl volumes at $2.5 \times 10^5$ cells per ml in a humidified incubator containing 5% $CO_2$ at 37° C. for 5 days. Fibrocytes were identified by morphology in viable cultures as adherent cells with an elongated spindle-shaped morphology as distinct from lymphocytes or adherent monocytes. Enumeration of fibrocytes was performed on cells cultured for 5 days. Cells were air dried, fixed in methanol and stained with eosin and methylene blue (Hema 3 Stain, Fisher Scientific, Hampton, N.H.). Fibrocytes from duplicate wells were counted in five different 900 µm diameter fields per well, using the above criteria of an elongated spindle-shape and the presence of an oval nucleus. All cultures were counted by at least two independent observers. The number of fibrocytes observed was $1.2 \pm 0.6 \times 10^4$ (mean±SD, n=12 healthy individuals) fibrocytes per ml of peripheral blood, with a range of $3.7 \times 10^3$ to $2.9 \times 10^4$ fibrocytes per ml. These results indicate that fibrocyte precursors account for approximately 1% of the total peripheral blood mononuclear cells.

Example 2

Antibodies, Proteins, and Inhibitors

Human IgA, IgG, IgM, and IgG F(ab')$_2$ fragments were from Jackson ImmunoResearch Laboratories, West Grove, Pa. Goat F(ab')$_2$ anti-human IgG, goat F(ab')$_2$ anti-murine IgG, goat F(ab')$_2$ anti-rabbit IgG, and whole mouse IgG1, whole mouse IgG2a and mouse F(ab')$_2$ IgG1 isotype control antibodies were from Southern Biotechnology Associates Inc., Birmingham, Ala. Sheep red blood cells (SRBC) and rabbit anti-SRBC were from ICN, Irvine, Calif. F(ab')$_2$ fragments of the blocking monoclonal antibodies to FcγRI (clone 10.1, IgG1 isotype) and FcγRII (clone 7.3, IgG1 isotype) were from Ancell, Bayport, Minn. The following primary monoclonal antibodies were used for immunohistochemistry: anti-CD14 (clone M5E2, IgG2a, BD-Biosciences, San Diego, Calif.), anti-CD34 (clone QBend10, IgG1, GeneTex, San Antonio, Tex.), CD 43 (clone IG10, IgG1, BD), pan-CD45 (clone H130, IgG1, BD), anti-prolyl 4-hydrolase (clone 5B5, IgG1, Dako, Carpinteria, Calif.), and anti-alpha smooth muscle actin (clone 1A4, IgG2a, Sigma-Aldrich, St. Louis, Mo.). Collagen-I was detected using an affinity-purified rabbit polyclonal antibody from Rockland, Gilbertsville, Pa. PP2 (AG 1879; 4-Amino-5-(4-chlorophenyl)-7-(t-butyl) pyrazolo[3,4-d]pyrimidine), PP3 4-Amino-7-phenylpyrazol [3,4-d]pyrimidine) and the Syk inhibitor (3-(1-Methyl-1H-indol-3-yl-methylene)-2-oxo-2,3-dihydro-1H-indole-5-sulfonamide) were from Calbiochem, EMD Biosciences, San Diego, Calif.

Example 3

Inhibition of Fibrocyte Differentiation

To determine if anti-FcγR antibodies activate FcγR to inhibit fibrocyte differentiation, PBMC at $2.5 \times 10^5$ per ml were cultured in serum-free medium for 5 days in the presence or absence of 1 µg/ml of free or cross-linked F(ab')$_2$ antibodies to FcγRI or FcγRII.

To crosslink individual FcγR, PBMC were incubated for 30 minutes at 4° C. with 1 µg/ml F(ab')$_2$ anti-FcγRI or F(ab')$_2$ anti-FcγRII, and receptors were then cross-linked by the addition of 500 ng/ml F(ab')$_2$ goat anti-mouse IgG for 30 minutes at 4° C. PBMC were then warmed to 37° C. and cultured for 5 days.

After the cells were cultured in the presence or absence of free or cross-linked F(ab')$_2$ antibodies to FcγRI or FcγRII, the cells were then air-dried, fixed, stained, and fibrocytes were enumerated by morphology. The results of this example are shown in FIG. 1.

Compared to PBMC cultured in the presence of 500 ng/ml goat F(ab')$_2$ anti-mouse IgG alone, cells cultured in the presence of 500 ng/ml goat F(ab')$_2$ anti-mouse IgG and anti-FcγRI or anti-FcγRII significantly inhibited fibrocyte differentiation ($p<0.01$, indicated by **), as determined by ANOVA (n=3 separate donors). These results suggest that cross-linking either FcγRI or FcγRII alone significantly inhibited fibrocyte differentiation. However, there was no additional inhibition when both receptors were cross-linked together, suggesting that no synergistic interaction occurs (FIG. 1). These experiments show that fibrocyte differentiation can be inhibited to approximately 50% by the addition of 1 µg/ml anti-FcγR. Greater inhibition could be achieved by incubating PBMC with higher concentrations of anti-FcγR (5 and 10 µg/ml), however these concentrations of anti-FcγR also led to significant cell death (data not shown). These results suggest that ligation and cross-linking of FcγRI or FcγRII can inhibit fibrocyte differentiation.

Figure 3:
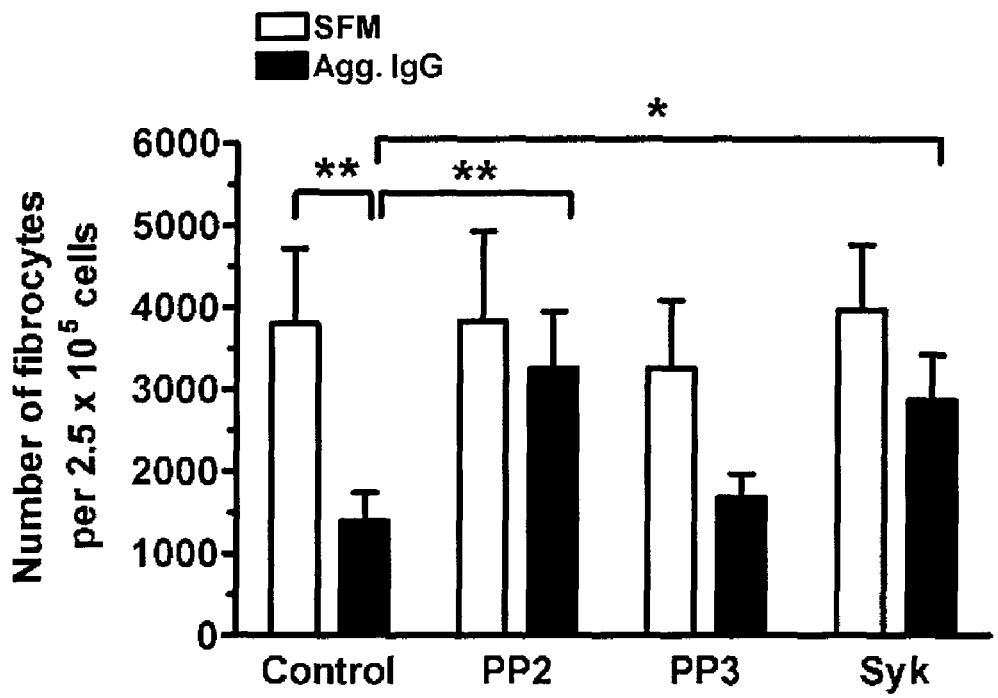
FIG. 3 shows the effects of FcγR aggregation and the effects of SRTK and Syk on fibrocyte differentiation from monocytes. PBMC were at $2.5\times10^5$ cells per ml were incubated for 60 minutes at 37° C. Non-adherent cells were then removed by pipetting, resulting in a substantially monocyte cell sample. The adherent monocytes were incubated for 60 minutes at 4° C. in the presence or absence of 10 nM PP2, PP3 or Syk inhibitor. Monocytes were then washed twice and cultured in the presence or absence of heat-aggregated human IgG for 60 minutes at 4° C. This IgG was not an anti-FcγR IgG, but instead was able to bind through its Fc region. The monocytes were then washed twice, and the non-adherent cells were replaced to a final concentration of $2.5\times10^5$ cells per ml and then cultured for 5 days at 37° C. in serum-free medium. Results are expressed as the mean±SEM of the number of fibrocytes per $2.5\times10^5$ cells (n=3 separate donors).

Although PBMC may contain various cells that may form fibrocytes, including monocytes, monocyte cultures alone may also differentiate to form fibrocytes. This phenomenon is show in FIG. 3. FIG. 3 also indicates that this fibrocyte differentiation is suppressed by the aggregation of FcγR. Specifically, compared to monocytes cultured in serum free medium (SFM), aggregated human IgG was able to cross-link FcγR through its Fc region significantly inhibited fibrocyte differentiation ($p<0.01$), as determined by ANOVA.

Example 4

Inhibition of Fibrocyte Differentiation is SYK- and SRC Kinase Dependent

FcγR activation leads to a cascade of signaling events initiated by two main kinases. The initial events following FcγR aggregation involve the phosphorylation of intracellular immunoreceptor tyrosine activation motifs (ITAM) present on the cytoplasmic tail of FcγRII or the FcRγ chain associated with FcγRI, by src-related tyrosine kinases (SRTK). In monocytes, the main src-kinases associated with FcγRI and FcγRII are hck and lyn. The phosphorylated ITAM then recruits cytoplasmic SH2-containing kinases, especially Syk, to the ITAMs and Syk then activates a series of downstream signaling molecules.

To determine the roles of SRTK and Syk in the regulation of fibrocyte differentiation, PBMC were pre-incubated with the specific SRTK inhibitor PP2, PP3 as a control for PP2, or the specific Syk inhibitor 3-(1-methyl-1H-indol-3-yl-methylene)-2-oxo-2,3-dihydro-1H-indole-5-sulfonamide, before the addition of anti-FcγR antibodies. This Syk inhibitor was used instead of the standard Syk inhibitor piceatannol, as piceatannol at concentrations used to inhibit Syk in whole cells (10 μM) also inhibits a variety of other enzymes and transcription factors. These proteins include the catalytic subunit of protein kinase A, protein kinase C, myosin light chain kinase, TNF-induced NF-kB activation, and interferon α-mediated signaling via STAT proteins.

Figure 2:
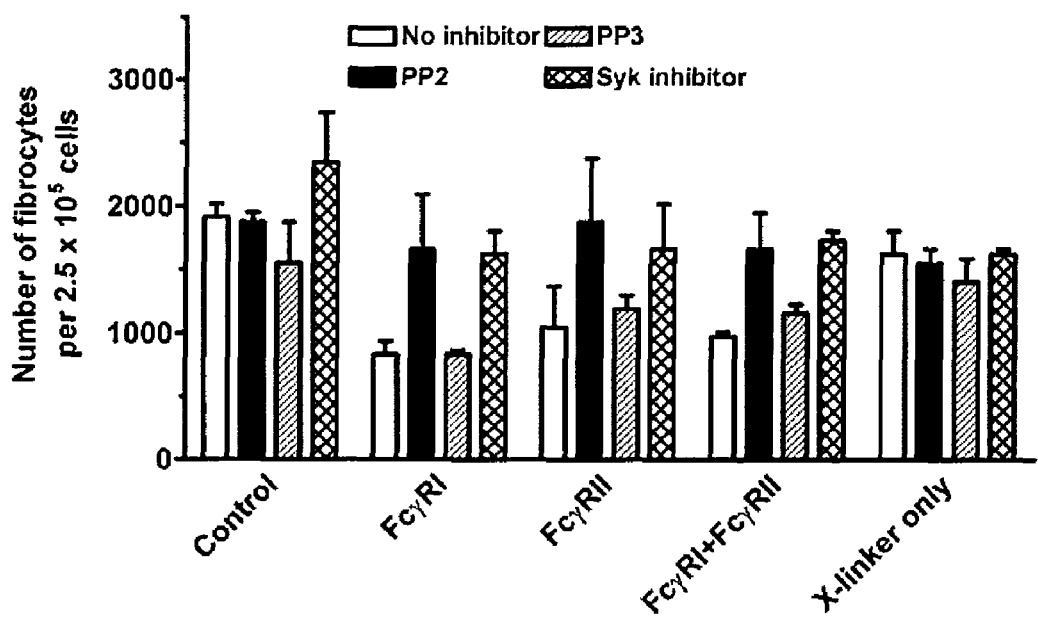
FIG. 2 shows the effects of SRTK and Syk inhibitors on the ability of anti-FcγR antibodies on fibrocyte differentiation from PBMC. PBMC were incubated for 60 minutes at 4° C. with 10 nM PP2, PP3, or Syk inhibitor. PBMC at $2.5\times10^5$ cells per ml were then cultured in serum-free medium for 5 days in the presence or absence of 1 µg/ml of the indicated murine $F(ab')_2$ anti-FcγR antibodies, in the presence or absence of 500 ng/ml goat $F(ab')_2$ anti-mouse IgG. Results are expressed as the mean±SD of the number of fibrocytes per $2.5\times10^5$ cells (one of two separate donors).

Inhibition of fibrocyte differentiation by activating either FcγRI or FcγRII alone or both receptors together was dependent on STRK and Syk, as the inhibition was lost when PBMC were pre-incubated with either PP2 or the Syk inhibitor (FIG. 2). Compared to control cultures or cultures incubated with of 500 ng/ml goat F(ab')$_2$ anti-mouse IgG (X-linker only), PBMC cultured with 500 ng/ml goat F(ab')$_2$ in addition to anti-mouse IgG anti-FcγRI, anti-FcγRII or both antibodies significantly inhibited fibrocyte differentiation ($p<0.05$), as determined by ANOVA. The presence of PP2 or Syk inhibitor, but not the control compound PP3, inhibited this inhibition. These data suggest that anti-FcγR antibodies inhibit fibrocyte differentiation through a pathway involving both Syk and SRTK.

Similar results were found when monocyte samples, rather than PBMC were used to perform tests. Specifically, in FIG. 3, compared to monocytes incubated with 10 μg/ml aggregated human IgG (able to bind to FcγR through its Fc region), pre-incubation with PP2 ($p<0.01$) or Syk inhibitor ($p<0.05$) significantly inhibited the ability of IgG to inhibit fibrocyte differentiation as determined by ANOVA.

Example 5

IgG Immune Complexes Inhibit Fibrocyte Differentiation

Figure 4A:
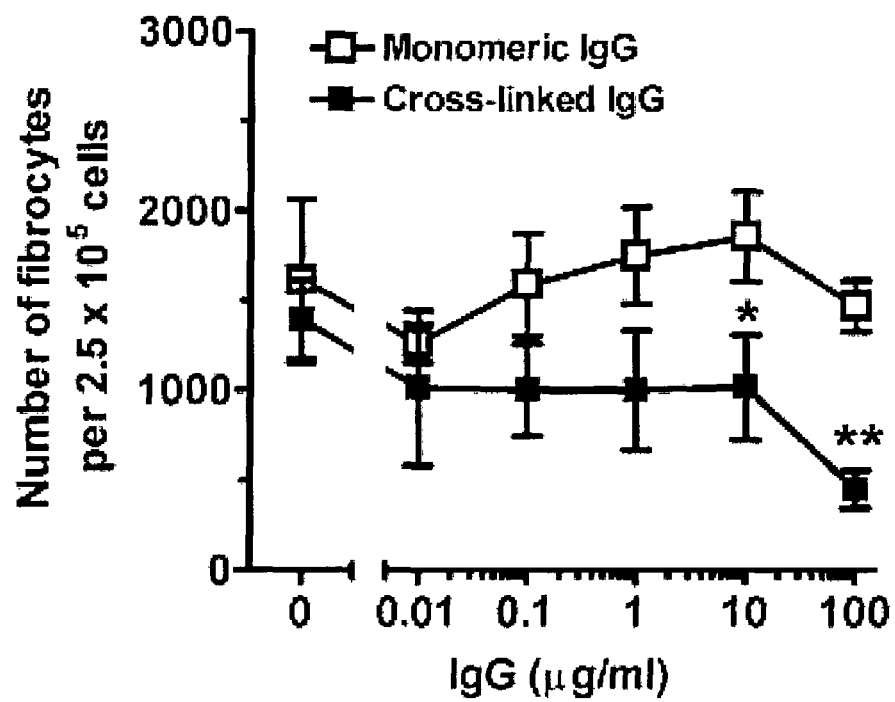
In FIG. 4A, PBMC were incubated with the indicated concentrations of monomeric human IgG for 60 minutes. PBMC were then washed and incubated in the presence (white boxes) or absence (black boxes) of 500 ng/ml goat F(ab')2 anti-human IgG. PBMC were then cultured at $2.5\times10^5$ cells per ml in serum-free medium for 5 days. PBMC were then air-dried, fixed, stained, and fibrocytes were enumerated by morphology. Results are expressed as the mean±SEM of number of fibrocytes per $2.5\times10^5$ cells (n=4 separate donors).
Figure 4B:
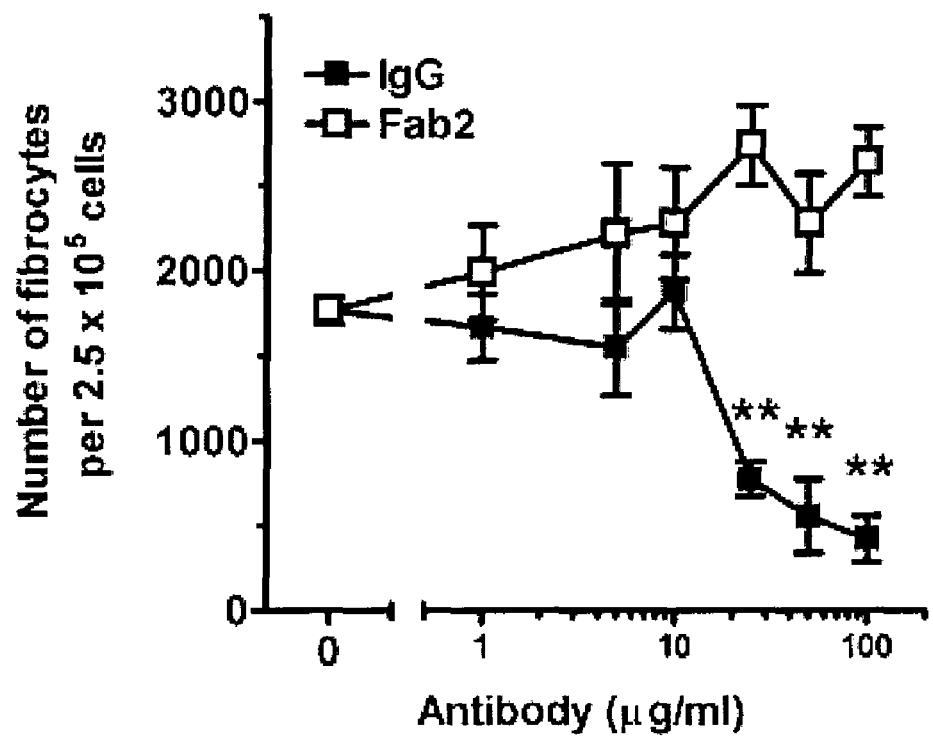
In FIG. 4B, PBMC were cultured as in FIG. 4A in the presence of the indicated concentrations of heat-aggregated human IgG or heat-aggregated human $F(ab')_2$. Results are expressed as the ±SEM of number of fibrocytes per $2.5\times10^5$ cells (n=3 separate donors).
Figure 4C:
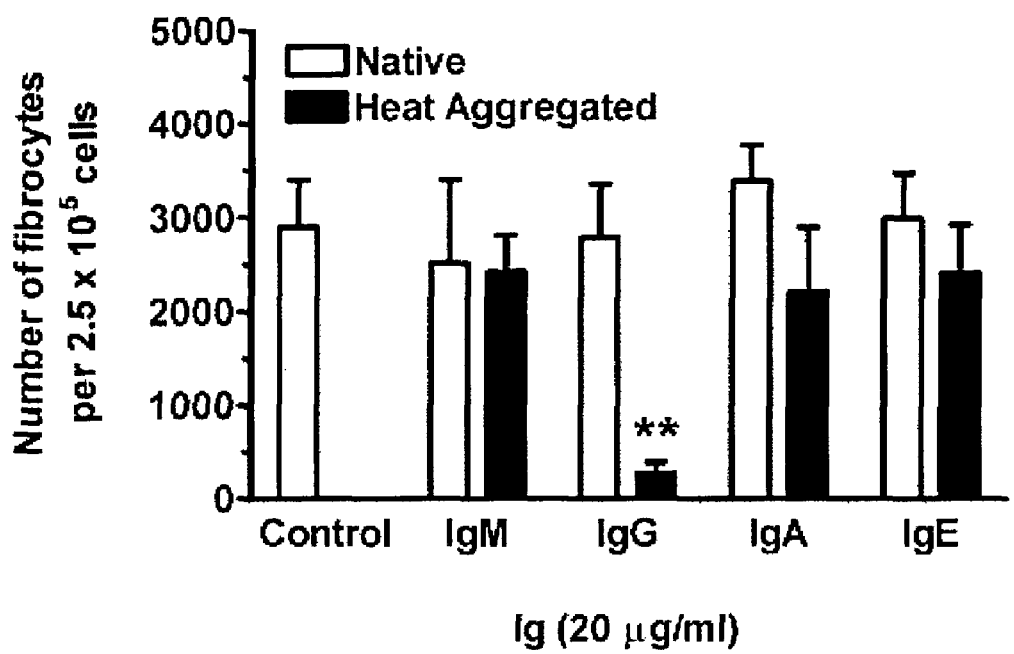
In FIG. 4C, PBMC were cultured as in FIG. 4A in the presence of 20 µg/ml of native or heat-aggregated human IgA, IgE, IgG or IgM.

In addition to FcγR, monocytes express IgA receptors, low numbers of IgE receptors, and the recently characterized IgM receptor. To determine if other immunoglobins inhibit fibrocyte differentiation, native or heat-aggregated IgA, IgE, IgG or IgM were added to PBMC. The results of this example are shown in FIG. 4C. Only heat-aggregated IgG, but not monomeric IgG or monomeric or heat-aggregated IgA, IgE or IgM, could inhibit fibrocyte differentiation. This suggests that ligation and cross-linking of FcγR receptors is an inhibitory signal for fibrocyte differentiation, but that ligation of the other immunoglobin receptors has no effect on fibrocyte differentiation.

Example 6

Cross-Linked IgG Inhibits Fibrocyte Differentiation

PBMC were incubated with the indicated various concentrations of monomeric human IgG for 60 minutes. PBMC were then washed and incubated in the presence or absence of 500 ng/ml goat F(ab')2 anti-human IgG. PBMC were then cultured at $2.5 \times 10^5$ cells per ml in serum-free medium for 5 days. PBMC were then air-dried, fixed, stained, and fibrocytes were enumerated by morphology. Results are shown in FIG. 4A. Specifically, compared to monomeric IgG, cross-linked human IgG clearly inhibited fibrocyte differentiation as compared to non-cross-linked IgG at 0.1 μg/ml. At 10 and 100 μg/ml inhibition of differentiation was significant ($p=0.03$ and $p=0.003$, respectively, as determined by Student's t test. Additional experiments using sheep red blood cells (SRBC) either opsinized or not opsinized with rabbit anti-SRBC IgG indicated that the opsinized SRBC significantly inhibited fibrocyte differentiation ($p=0.018$) (data not shown).

PBMC were also cultured as above in the presence of the indicated concentrations of heat-aggregated human IgG or heat-aggregated human F(ab')$_2$. Results of this example are shown in FIG. 4B. Compared to heat-aggregated human F(ab')$_2$, heat-aggregated whole IgG significantly inhibited fibrocyte differentiation at concentrations of 25 μg/ml and higher, as determined by Student's t test.

Although only exemplary embodiments of the invention are specifically described above, it will be appreciated that modifications and variations of these examples are possible without departing from the spirit and intended scope of the invention.

Example 7

Antibody Studies

Figure 5:
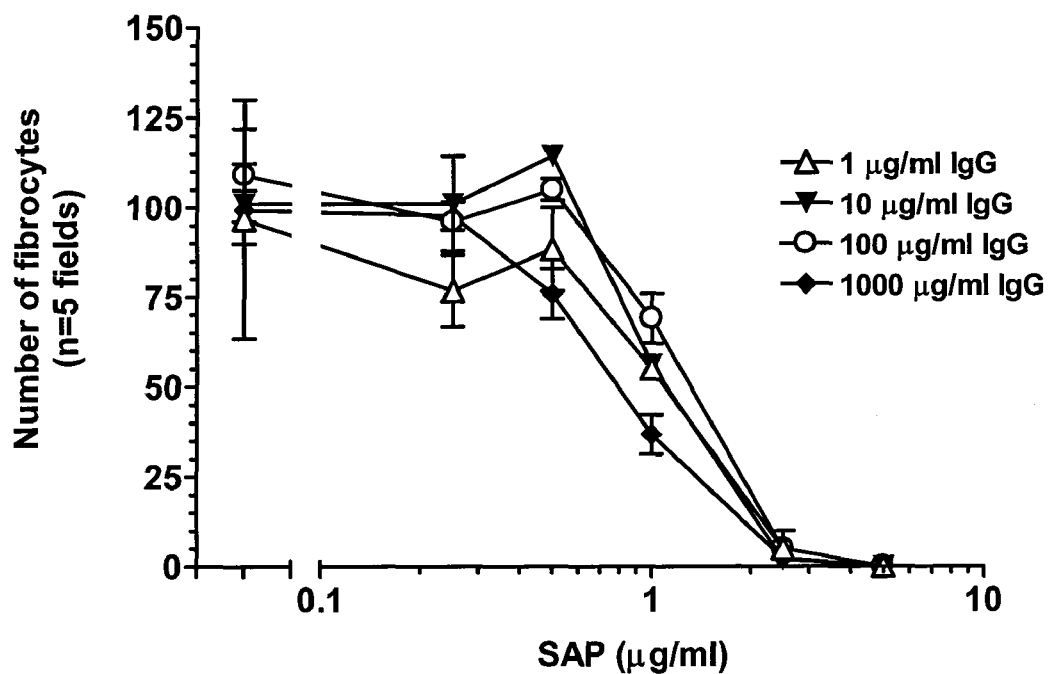
FIG. 5 shows the effects of monomeric IgG on the ability of SAP to bind to monocytes and inhibit their differentiation. PBMC were cultured in serum-free medium in the presence of a range of concentrations of monomeric IgG for 60 minutes. SAP, at the concentrations indicated, was then added and the cells were cultured for 4 days.

SAP and CRP augment phagocytosis and bind to Fcγ receptors on a variety of cells. CRP binds with a high affinity to FcγRII (CD32), a lower affinity to FcγRI (CD64), but does not bind FcγRIII (CD16). SAP binds to all three classical Fcγ receptors, with a preference for FcγRI and FcγRII. Monocytes constitutively express FcγRI. Because this receptor binds monomeric IgG, it is saturated in vivo. In order to determine whether the presence of monomeric human IgG could prevent SAP from inhibiting fibrocyte differentiation, PBMC were cultured in serum-free medium in the presence of a range of concentrations of monomeric IgG for 60 minutes. SAP, at the concentrations indicated in FIG. 5, was then added and the cells were cultured for 4 days. As described in the above examples, 2.5 μg/ml SAP in the absence of IgG strongly inhibited fibrocyte differentiation. (See FIG. 5.) Monomeric IgG in a range from 0.1 to 1000 μg/ml, which corresponds to approximately 0.001 to 10% serum respectively, had little effect on the suppression of fibrocyte formation by SAP.

Figure 6A:
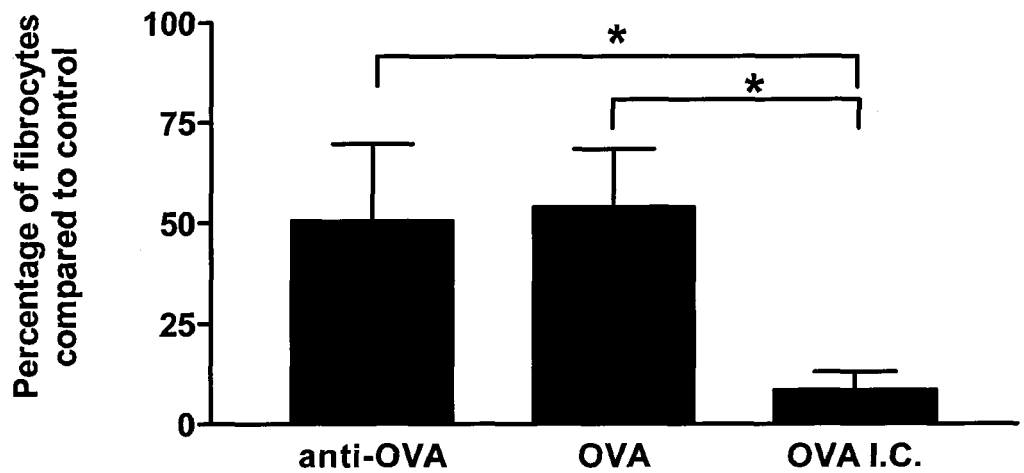
In FIG. 6A PBMC cultured for 4 days with ovalbumin or anti-ovalbumin mAb alone, or ovalbumin:anti-ovalbumin immune complexes.
Figure 6B:
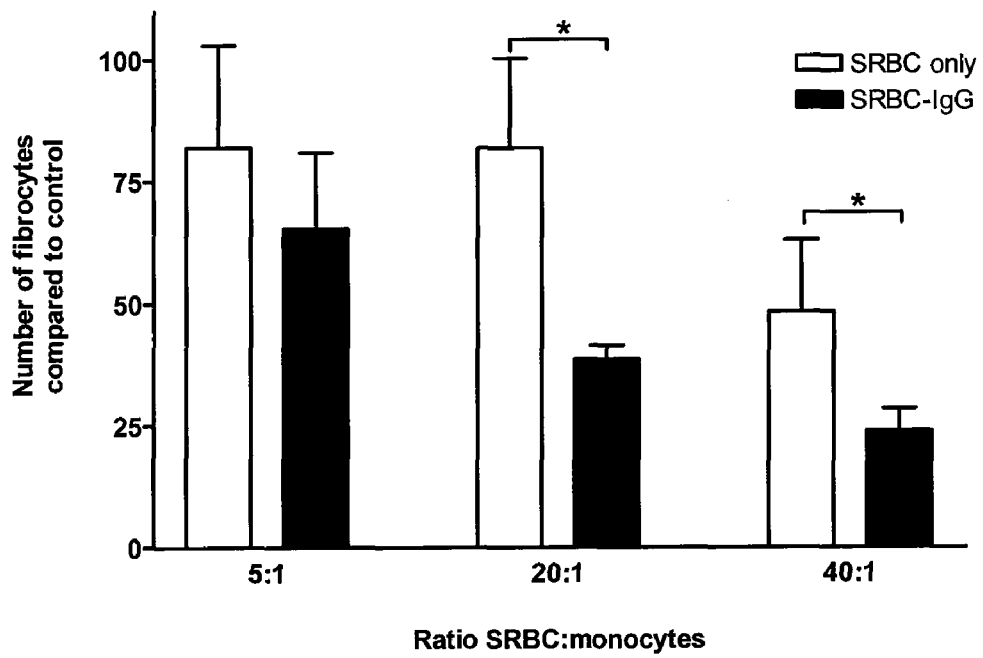
FIG. 6B shows the effects of SRBC alone and SRBC opsonised with rabbit anti-SRBC at 20:1 and 40:1 SRBC: monocyte ratios. Finally.
Figure 6C:
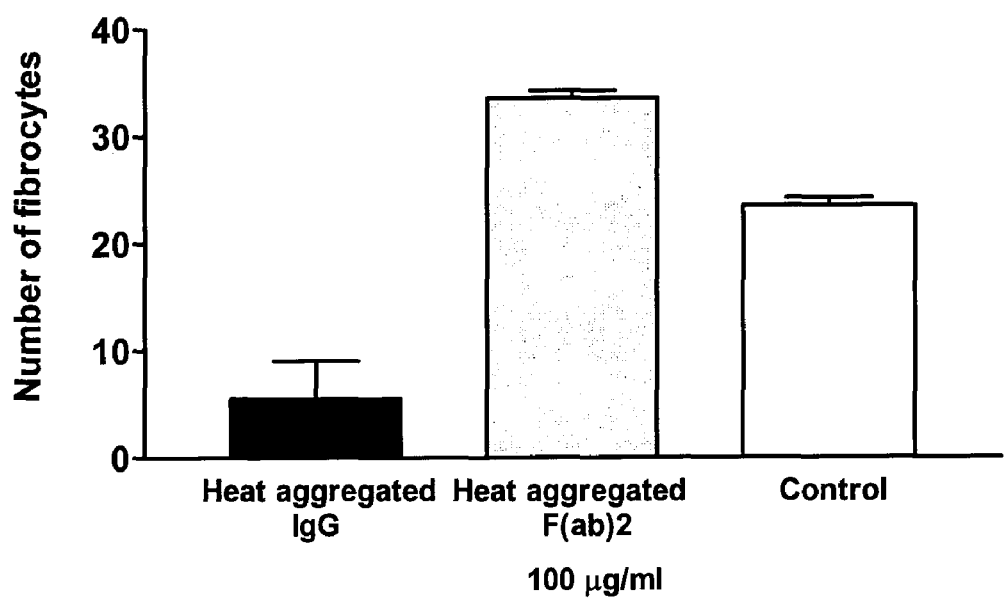
FIG. 6C shows the effects on PBMC of heat-aggregated IgG and heat-aggregated $F(ab)_2$. Stars in 6A and 6B indicate statistically significant differences.

To determine whether ligation and cross-linking of Fc receptors could also influence monocyte to fibrocyte differentiation, three test samples were used; soluble immune complexes (ovalbumin-antibody), particulate immune complexes, including opsonised SRBC and heat-aggregated IgG. PBMC cultured for 4 days with ovalbumin or anti-ovalbumin mAb showed that the two proteins alone had a modest effect on the differentiation of monocytes compared to cultures where no reagent was added. (See FIG. 6A.) However, the addition of ovalbumin:anti-ovalbumin immune complexes led to a significant reduction in the number of differentiated fibrocytes (See FIG. 6A). A similar effect was observed when PBMC were cultured with opsonised SRBC. SRBC opsonised with rabbit anti-SRBC at 20:1 and 40:1 SRBC:monocyte ratios significantly suppressed fibrocyte differentiation as compared to cells cultured with SRBC alone (See FIG. 6B). Finally, PBMC cultured with heat-aggregated IgG, but not heat-aggregated F(ab)₂, also showed potent inhibition of fibrocyte differentiation (See FIG. 6C.) Together these data suggest that ligation and cross-linking of Fc receptors is suppressor of monocyte to fibrocyte differentiation.

Figure 7:
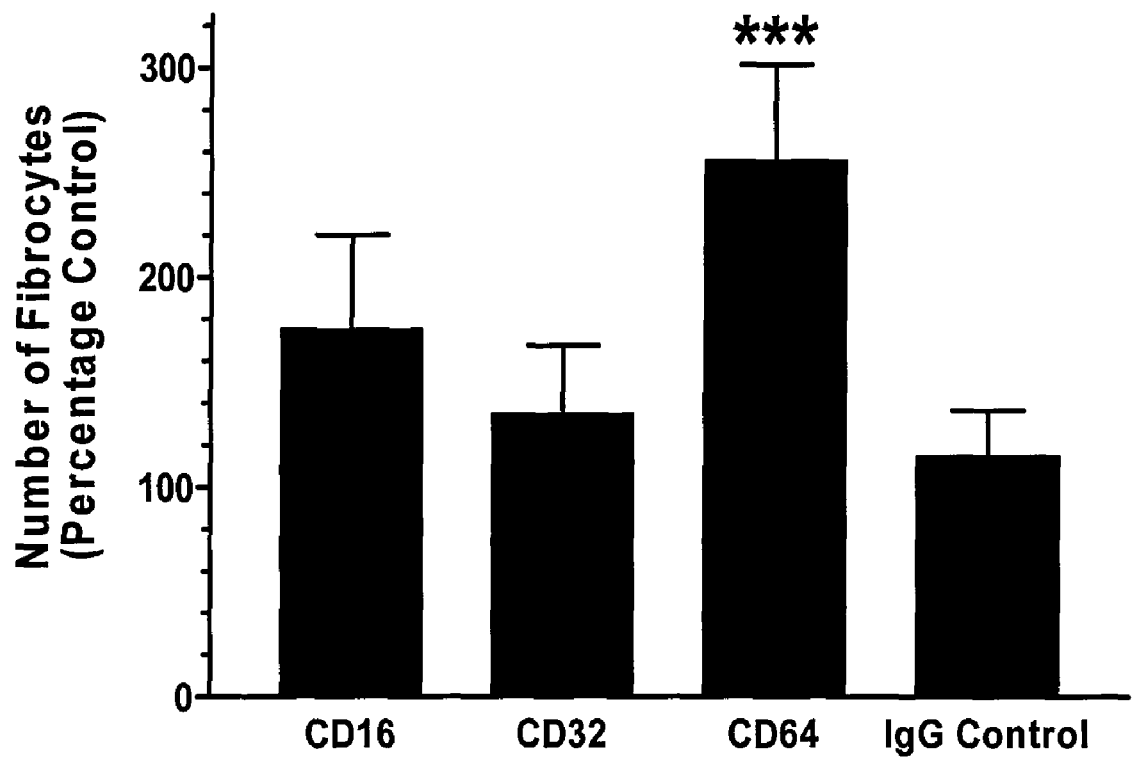
FIG. 7 shows the effects of anti-FcγR antibodies on monocyte differentiation. Stars indicate a statistically significant difference from control.

The observation that immune complexes inhibit fibrocyte differentiation suggests that one or more FcγR influences fibrocyte differentiation. To examine the role of FcγR in fibrocyte differentiation PBMC were cultured in the presence or absence of blocking antibodies to FcγRI (CD64), FcγRII (CD32) or FcγRIII (CD16) before the addition of SAP, or as a control CRP. When samples were pre-incubated with a blocking mAb for each of the three FcγR, SAP was later able to modestly suppress fibrocyte differentiation. However, in the absence of exogenously added SAP, the FcγRI (CD64) blocking mAb had a profound effect on fibrocyte differentiation. Incubation of PBMC with blocking mAb to FcγRI, but not FcγRII or FcγRIII, promoted fibrocyte differentiation as compared to cells cultured with isotype-matched control mAb or cells cultured with no mAb (P<0.01) (See FIG. 7). These data suggested that SAP or IgG, might have been produced by some cells in the culture system over 4 days, or that SAP or IgG was retained by cells from the blood. Western blotting failed to show the presence of SAP or IgG after cells had been cultured for 4 days in vitro. This suggests that the FcγRI blocking mAb has a direct effect on fibrocyte differentiation or that SAP or IgG were only present during the early time points of the cell culture.

The invention claimed is:

1. A method of suppressing fibrocyte formation in a subject in need thereof comprising administering to the subject having pulmonary fibrosis an anti-FcγR antibody in an amount sufficient to suppress fibrocyte formation in a lung.

2. The method of claim 1, wherein the anti-FcγR antibody is administered at a concentration of at least 1.0 µg/ml.

3. The method of claim 1, wherein the anti-FcγR antibody is administered at a concentration of at least 0.1 µg/ml.

4. The method of claim 1, wherein the antibody is an IgG.

5. The method of claim 1, wherein the antibody is an anti-FcγRI antibody.

6. The method of claim 1, wherein the antibody is an anti-FcγRII antibody.

7. The method of any one of claims 4-6, wherein the antibody comprises an F(ab')₂ fragment.

8. The method of any one of claims 4-6, wherein the antibody comprises an Fc fragment.

9. The method according to claim 1, wherein the pulmonary fibrosis comprises a condition selected from the group consisting of: Adalimumab-associated pulmonary interstitial fibrosis, sarcoidosis, idiopathic pulmonary fibrosis, asthma, chronic obstructive pulmonary disease, diffuse alveolar damage disease, pulmonary hypertension, neonatal bronchopulmonary dysplasia, and emphysema.

10. The method of claim 1, wherein the antibody is an anti-FcγRIII antibody.

* * * * *